(12) United States Patent
Karau et al.

(10) Patent No.: US 7,447,341 B2
(45) Date of Patent: Nov. 4, 2008

(54) METHODS AND SYSTEMS FOR COMPUTER AIDED TARGETING

(75) Inventors: Kelly Lynn Karau, New Berlin, WI (US); Saad Ahmed Sirohey, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 676 days.

(21) Appl. No.: 10/722,974

(22) Filed: Nov. 26, 2003

(65) Prior Publication Data

US 2005/0113960 A1 May 26, 2005

(51) Int. Cl.
*G06K 9/00* (2006.01)
(52) U.S. Cl. .................. 382/128; 382/131; 382/199; 382/259; 382/130; 382/299; 378/8; 378/62; 378/4; 378/901; 600/425; 600/547; 600/437
(58) Field of Classification Search ............. 382/284, 382/128, 299, 131, 199, 259, 130; 378/62, 378/8, 4, 901; 600/407, 425, 547, 437; 345/103
See application file for complete search history.

(56) References Cited

U.S. PATENT DOCUMENTS

| | | | |
|---|---|---|---|
| 6,453,058 B1 | 9/2002 | Murthy et al. | |
| 6,574,304 B1 * | 6/2003 | Hsieh et al. | 378/62 |
| 6,628,815 B2 * | 9/2003 | Wang | 382/132 |
| 6,678,399 B2 * | 1/2004 | Doi et al. | 382/131 |
| 6,687,329 B1 * | 2/2004 | Hsieh et al. | 378/62 |
| 7,054,473 B1 * | 5/2006 | Roehrig et al. | 382/128 |
| 7,072,435 B2 * | 7/2006 | Metz et al. | 378/8 |
| 2002/0054697 A1 * | 5/2002 | Wang | 382/128 |
| 2005/0090745 A1 * | 4/2005 | Steen | 600/447 |
| 2005/0228280 A1 * | 10/2005 | Ustuner et al. | 600/443 |
| 2006/0245536 A1 * | 11/2006 | Boing et al. | 378/8 |
| 2006/0256111 A1 * | 11/2006 | Chihoub et al. | 345/424 |
| 2007/0237295 A1 * | 10/2007 | Gundel | 378/62 |

OTHER PUBLICATIONS

Volume Pro Principles of Operation, TeraRecon, Inc., part No. 81-0005, Dec. 2001.*

* cited by examiner

*Primary Examiner*—Andrew W. Johns
*Assistant Examiner*—Nancy Bitar
(74) *Attorney, Agent, or Firm*—Armstrong Teasdale LLP

(57) ABSTRACT

A method for acquiring an image on an imaging system includes accessing at least first image data from a first imaging system, processing the first image data in accordance with a CAD algorithm, acquiring at least second image data based upon results of the CAD algorithm and processing the second image data in accordance with the CAD algorithm to confirm the results of the CAD algorithm regarding the first image data.

12 Claims, 2 Drawing Sheets

METHODS AND SYSTEMS FOR COMPUTER AIDED TARGETING

BACKGROUND OF THE INVENTION

This invention relates generally to imaging procedures, and more particularly to methods and apparatus for improving computer aided detection or diagnosis by utilizing a computer aided processing technique.

Computer aided diagnosis (CAD), such as screening mammography and evaluation of other disease states or medical or physiological events, is typically based upon various types of analysis of a series of collected images. The collected images are analyzed by utilizing the pathologies that are highlighted by a CAD algorithm. The results are generally viewed by radiologists for final diagnosis. As can be appreciated by those skilled in the art, certain subsequent imaging procedures may become feasible or may be recognized as desirable due to the improved management of data volume.

It should be noted that CAD may be utilized in any imaging modality, such as computed tomography (CT), magnetic resonance imaging (MRI), X-ray systems, ultrasound systems, positron emission tomography (PET), and so forth. CAD algorithms in certain of these modalities may provide advantages over those in other modalities, depending upon the imaging capabilities of the modality, the tissue being imaged, and so forth. Computed tomography, for example, is generally a diagnostic procedure in which cross-sectional images or slices are made by an X-ray system. The CT scanning procedure combines the use of a computer system and a rotating X-ray device to create detailed cross sectional images or "slices" of a patient's organs and other body parts. The imaging capabilities are physically similar to those of X-ray systems. MRI, ultrasound, PET, and other modalities similarly are adapted to imaging certain tissues or anatomies, and provide advantages for the different CAD algorithm employed with images they produce.

Each imaging modality is based upon unique physics and image processing techniques. For example, a CT system measures the attenuation of X-ray beams passed through a patient from numerous angles, and then, based upon these measurements, a computer is able to reconstruct images of the portions of a patient's body responsible for the radiation attenuation. As will be appreciated by those skilled in the art, these images are based upon separate examination of a series of continuous cross sections. Thus, a virtual 3-D image may be produced by a CT examination. It should be pointed out that a CT system does not actually directly provide an image, but rather numerical values of tissue density. The image based upon the reconstructed data is typically displayed on a cathode ray tube, and may be printed or reproduced on film.

Continuing with the example of CT imaging, CT scanners operate by projecting fan shaped X-ray beams from an X-ray source that is collimated and passes through the object, such as a patient, that is then detected by a detector element. The data is then used to produce a useful image. Thus, the detector element produces data based on the attenuation of the X-ray beams, and the data are processed by computer analysis. The locations of pathologies may then be highlighted by the CAD algorithm, and thus brought to a human observer's attention. A radiologist or other physician for final diagnosis may then review the results.

Each imaging modality may provide unique advantages over other modalities for certain types of disease or physiological condition detection. For example, CT scanning provides advantages over other types of techniques in diagnosing disease particularly because it illustrates the shape and exact location of organs, soft tissues, and bones for any slice of the body. Further, CT scans may help doctors distinguish between a simple cyst, for example, and a solid tumor, and thus evaluate abnormalities more accurately. As mentioned above, other imaging modalities are similarly best suited to imaging other physiological features of interest, and to corresponding CAD algorithms.

Existing techniques for computerized diagnosis of physiological features suffer from certain drawbacks. For example, the output of the CAD analysis is generally fairly, interactive, requiring assessment and evaluation by a seasoned practitioner. Due to time constraints and the availability of such persons, a patient is often called upon to report for certain types of examination, with further examinations needing to be scheduled, when appropriate, based upon the review of the CAD analysis. That is to say, patients often must return for additional tests on the same or a different modality imaging system in order to properly evaluate and diagnose potential conditions. The resulting procedure is not only time-consuming for the patient and for the physician, but ultimately results in the entire process extending over a considerable period of time. Additional appointments for subsequent imaging can also result in considerable expense both for the patient, for hospitals and clinics, and for insurance carriers.

For example, thin slice, high-resolution, CT (HRCT) scanner technology generates magnitudes of axial and volumetric data that requires significant time for radiologists to review. This demanding of more time from the radiologist may lessen the number of exams he or she can complete on a daily basis. Additionally, the radiologist's responsibility for high sensitivity to a vast amount of information presented in HRCT images may be threatening and may even discourage radiologists from performing screening (or therapy follow-up) studies in the first place. An answer to this explosion of data and patient management has been computer-assisted detection (CAD) of features of interests (FOIs) within image volumes. As a second-reviewer (complementing the initial radiologist review) CAD provides assistance to radiologists by setting markers where gray-levels in the CT image are unexpected, match a distinctive pattern, or do not appear as might be typically expected in a healthy individual.

Whether a FOI is detected by a CAD system or by a radiologist (or the combination of both), the critical step toward informed clinical management of that feature is in accurate segmentation (from other anatomic or pathologic structures) and quantification (volumetric, densitometric, functional, geometric, etc.). Since the release of applications such as Advanced Lung Analysis (ALA), it has been learned that the ability to accurately determine the volumetric size of small objects depends on the scan-acquisition and reconstruction variables used in generating an image volume. Considerable variability in segmentation and sizing of small features may be introduced due to partial-volume effects inherent to multi-slice CT scanner acquisition, patient motion, and misregistration. Therefore, it is advisable to perform a targeted reconstruction at a small display field of view and optimal reconstruction parameters to capture maximum detail from a detected FOI. Unfortunately, at the time the radiologist reviews (and detects) a FOI in a typical screening exam, the raw projection (scan) data has been overwritten or removed from the CT console and thus, retrospective acquisition of projection data is no longer an option. Additionally, sometimes the CAD analysis results in a false positive.

BRIEF DESCRIPTION OF THE INVENTION

In one aspect, a method for acquiring an image on an imaging system is provided. The method includes accessing at least first image data from a first imaging system, processing the first image data in accordance with a CAD algorithm, acquiring at least second image data based upon results of the CAD algorithm and processing the second image data in accordance with the CAD algorithm to confirm the results of the CAD algorithm regarding the first image data.

In another aspect, a method for acquiring an image on an imaging system is provided. The method includes receiving an indication of examination type prior to any image data acquisition operation, accessing at least first image data from a first imaging system, processing the first image data in accordance with a CAD algorithm, acquiring at least second image data based upon results of the CAD algorithm, and post-processing the second image data based on the received examination type without operator intervention.

In yet another aspect, a method for acquiring an image on an imaging system is provided. The method includes accessing at least first image data from a first imaging system using a first scan prescription, processing the first image data in accordance with a CAD algorithm, prompting a user to prescribe a second scan prescription different than the first scan prescription based upon results of the CAD algorithm, and acquiring at least second image data using the second scan prescription.

In still another aspect, a method for a seamless display and analysis of dual resolution image data is provided. The method includes reviewing image data at low resolution, performing a volumetric analysis of at least one feature of interest in the low resolution data, substituting high-resolution image data for analyzed low resolution data without operator intervention, and displaying a volume rendering of the low resolution data and analysis results of the high-resolution data in a single display.

In one aspect, an imaging system includes a first image data acquisition system configured to acquire medical images, and a computer coupled to the image data acquisition system and configured to generate a first series of images from image data acquired by the acquisition system to process series of images via a CAD algorithm, to prescribe acquisition of a second series of images based upon results of the CAD algorithm, and to process the second series of images via the CAD algorithm to confirm the result of the CAD algorithm regarding the first series of images.

In another aspect, a computer program for acquiring medical image data is provided. The program includes a machine readable medium, and a computer program stored on the medium and including routines for receiving an indication of examination type prior to any image data acquisition operation, acquiring a first series of images from a first imaging system, processing the first series of images in accordance with a CAD algorithm, acquiring a second series of images based upon results of the CAD algorithms, and post-processing the second series of images based on the received examination type without operator intervention.

In still another aspect, a computer program for acquiring medical image data is provided. The program including a machine readable medium, and a computer program stored on the medium and including routines for receiving low resolution image data, performing a volumetric analysis of at least one feature of interest in the low resolution data, substituting high-resolution image data for analyzed low resolution data without operator intervention, and displaying a volume rendering of the low resolution data and analysis results of the high-resolution data in a single display.

In yet another aspect, an imaging system includes a first image data acquisition system configured to acquire medical images, and a computer coupled to the image data acquisition system. The computer is configured to receive low resolution image data, perform a volumetric analysis of at least one feature of interest in the low resolution data, substitute high-resolution image data for analyzed low resolution data without operator intervention, and display a volume rendering of the low resolution data and analysis results of the high-resolution data in a single display.

DETAILED DESCRIPTION OF THE INVENTION

Figure 1:
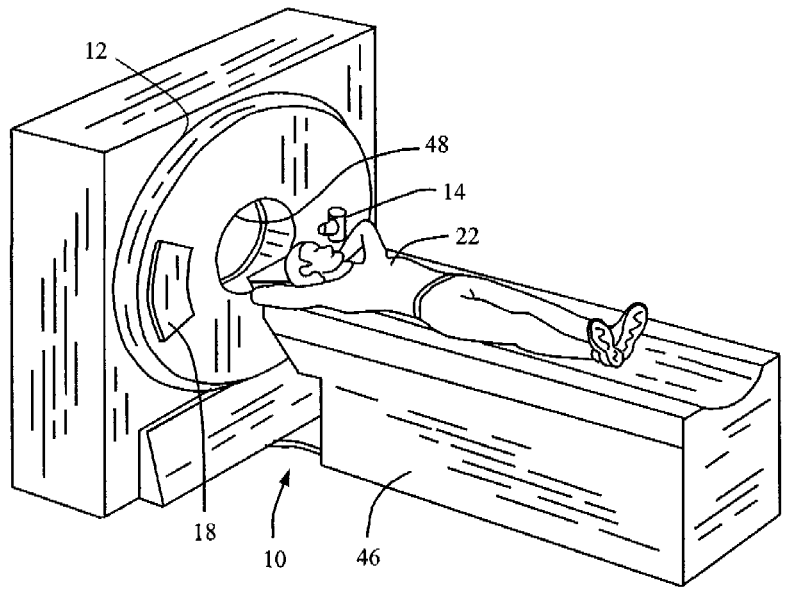
FIG. 1 is a pictorial view of a CT imaging system.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
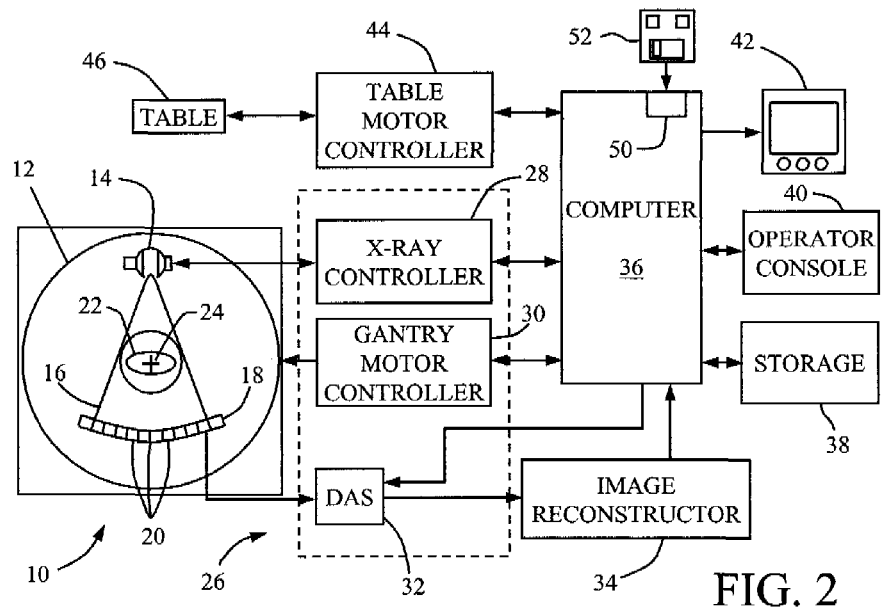
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via a console 40 (operator workstation) that has a keyboard, or other input device. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center. Additionally, while the herein described methods and systems refer to human patients, it is contemplated that the benefits of the invention accrue to systems sized to study animals.

The data collected by DAS 32 may be transmitted to computer 36 and moreover, to a memory (not shown). It should be understood that any type of memory to store a large amount of data may be utilized by such an exemplary system 10. Also, computer 36 is configured to receive commands and scanning parameters from an operator via console 40 typically equipped with a keyboard and other input devices. An operator may control the system 10 via the input devices. Thus, the operator may observe the reconstructed image and other data relevant to the system from computer 36, initiate imaging, and so forth.

Additionally, the scanned image may also be printed on to a printer (not shown) that may be coupled to computer 36 and operator workstation 40. Further, operator workstation 40 may also be coupled to a picture archiving and communications system (PACS). It should be noted that the PACS may be coupled to a remote system, a radiology department information system (RIS), a hospital information system (HIS) or to an internal or external network, so that others at different locations may gain access to the image and/or to the image data.

It should be further noted that computer 36 and console 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Once reconstructed, the image produced by the system of FIGS. 1 and 2 reveals internal features of a patient. In traditional approaches to diagnosis of medical conditions, such as disease states, and more generally of medical events, a radiologist or physician would consider a hard copy of display of an image to discern characteristic features of interest. Such features might include lesions, sizes and shapes of particular anatomies or organs, and other features that would be discernable in the image based upon the skill and knowledge of the individual practitioner.

The present technique implements certain of these capabilities by CAD algorithms. As will be appreciated by those skilled in the art, CAD algorithms may offer the potential for identifying, or at least localizing, certain features of interest, such as anatomical anomalies. The particular CAD algorithm is commonly selected based upon the type of feature to be identified, and upon the imaging modality used to create the image data. The CAD technique may employ segmentation algorithms, which identify the features of interest by reference to known or anticipated image characteristics, such as edges, identifiable structures, boundaries, changes or transitions in colors or intensities, changes or transitions in spectrographic information, and so forth. Current CAD algorithms generally offer the potential for identifying these features only. Subsequent processing and data acquisition is, then, entirely at the discretion and based upon the expertise of the practitioner.

CAD algorithms may be considered as including several parts or modules, all of which may be implemented in the present technique. In general, the CAD algorithm may include modules such as accessing image data, segmenting data or images, feature selection or extraction, classification, training, and visualization. Moreover, the CAD processing may be performed on an acquisition projection data set prior to reconstruction, on two-dimensional reconstructed data (both in axial and scout modes), on three-dimensional reconstructed data (volume data or multiplanar reformats), or a suitable combination of such formats. The acquired projection data set may have a number of one-dimensional projections for two-dimensional scans or a number of two-dimensional projections for three-dimensional scans. Using the acquired or reconstructed data, segmentation, feature selection, and/or classification prior to visualization may be performed. These processes can be done in parallel, or in various combinations.

The data on which the CAD algorithm is implemented may be raw image acquisition system information, or may be partially or completely processed data. The data may originate from a tomographic data source, or may be diagnostic tomographic data (such as raw data in projection or Radon domain in CT imaging, single or multiple reconstructed two-dimensional images, or three-dimensional reconstructed volumetric image data). Because the benefits of the invention accrue to different dimensional data, the term "area" as used herein refers to both two dimensional areas as well as three dimensional volumes.

The segmentation portion of the CAD algorithm may identify a particular region of interest based upon calculated features in the tomographic data. The region of interest can be determined in a number of manners, using an entire data set or using part of a data set, such as a candidate mass region in a specific area. The particular segmentation technique may depend upon the anatomies to be identified, and may typically be based upon iterative thresholding, K-means segmentation, edge detection, edge linking, curve fitting, curve smoothing, two- and three-dimensional morphological filtering, region growing, fuzzy clustering, image/volume measurements, heuristics, knowledge-based rules, decision trees, neural networks, and so forth. Alternatively, the segmentation may be at least partially manual. Automated segmentation may also use prior knowledge such as shape and size of a mass to automatically delineate an area of interest.

The feature extraction aspect of the CAD algorithm involves performing computations on the data that comprises the desired images. Multiple feature measures can be extracted from the image-based data using region of interest statistics, such as shape, size, density, and curvature. For projection space data, features such as location, shape, or size of feature projections in a view or location may be used, such as to provide consistency between views.

The classification aspects of the CAD algorithm may be, again, partially or fully manual or automated. In particular, the classification may be used to specifically identify regions of interest, such as by classification as normal or abnormal anatomies or lesions. Bayesian classifiers, neural networks, rule-based methods or fuzzy logic techniques, among others, can be used for classification. It should be noted that more than one CAD algorithm could be employed in parallel. Such parallel operation may involve performing CAD operations individually on portions of the image data, and combining the results of all CAD operations (logically by "and", "or" operations or both). In addition, CAD operations to detect multiple disease states or anatomical features of interest may be performed in series or in parallel.

Prior to classification of masses for anatomies using the CAD algorithm, prior knowledge from training may be incorporated. The training phase may involve the computation of several candidate features on known samples of normal and abnormal lesions or other features of interest. A feature selection algorithm may then be employed to sort through the candidate features and select only the useful ones and remove those that provide no information, or redundant information. This decision is based upon classification results with different combinations of candidate features. The feature selection algorithm may also be used to reduce the dimensionality for practical reasons of processing, storage and data transmission. Thus, optimal discrimination may be performed between features or anatomies identified by the CAD algorithm.

The visualization aspect of the CAD algorithm permits reconstruction of useful images for review by human or machine observers. Thus, various types of images may be presented to the attending physician or to any other person needing such information, based upon any or all of the processing and modules performed by the CAD algorithm. The visualization may include two- or three-dimension renderings, superposition of markers, color or intensity variations, and so forth.

Figure 3:
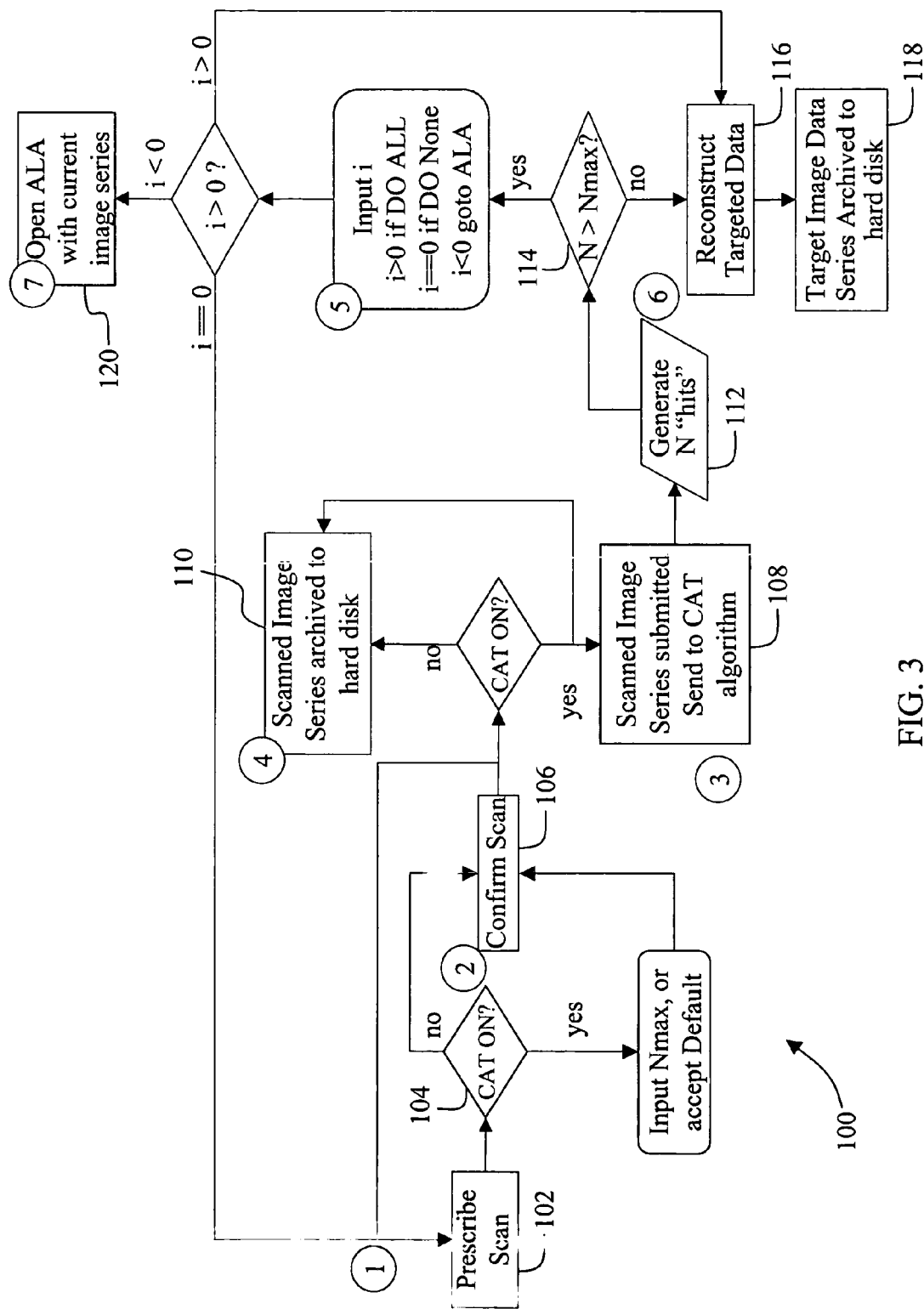
FIG. 3 is a flow chart illustrating a method to detect suspicious regions in imaging data.

FIG. 3 is a flow chart illustrating a method 100 to detect suspicious regions of the CT image volume in various types of CT (routine, high resolution, screening, etc.) examinations and automatically perform (1) Retrospective targeted reconstruction at small display field of view and optimal reconstruction parameters and/or (2) Prospective re-scanning for improved quantitative image quality in those regions.

In one embodiment, a computer assisted automated targeted reconstruction prospectively creates an alternative reconstruction (high-resolution, small display field of view, alternate reconstruction algorithm, filtering, slice thickness, etc.) of images encompassing the suspected anatomy or FOI found by a CAD algorithm. These images (alternate reconstructions) are then sent for a radiologist's review within the framework of a normal workflow. These additional images are accessible to the radiologist in a seamless manner for review by providing the following.

(a) Access to the high resolution images (when available) when the radiologist wants to better visualize using volume rendering with segmentation, or quantify by determining the volume etc.

(b) An additional source of productivity improvement, wherein the segmentation and volumetric measurements prescribed prior to the scan and made available for the reader at the time of review. For example, when the user knows what quantitative information will be desired from the FOI, that information is requested prior to the scan and the full processing chain is executed with results being available at the time of review and will save time from post-processing at the review client. For example, computer 36 receives an indication of examination type prior to any image data acquisition operation, accesses at least first image data from a first imaging system, processes the first image data in accordance with a CAD algorithm, acquires at least second image data based upon results of the CAD algorithm, and post-processes the second image data based on the received examination type without operator intervention. Then the post-processed second image, a post-processed first image, and the exam type is provided to a reader who may be at the exam site itself or at a remote site.

(c) As a third review opportunity, the retrospectively reconstructed targeted image series may be re-submitted to the CAD algorithm for further review and refinement in order to confirm the detections (i.e., results of the CAD analysis on the initial scan) based on evaluation of the high-resolution data.

(d) The radiologist can also directly view the data with visualization techniques other than axial images (for example, 3D reformatted views) at the time of review.

(e) The retrospectively reconstructed images are automatically linked with their initial (perhaps thicker slice CT data) image acquisition so that access to the alternate data types is seamless through the workflow.

In another embodiment, a radiologist requested targeted reconstruction that may be needed for better visualization and/or quantification of a FOI that has been identified by the radiologist. This is requested at the CT console, at a reviewing workstation that is networked to the CT scanner, or at any local or peripheral client or access point to the CT scanner in accordance with the following.

(a) When the radiologist request is made at the CT Console, the request is serviced immediately from the CT scan data available and this data is made available through appropriate notification and user interface at the console.

(b) When the request is made from a networked workstation, this involves communicating the request over the network, having the scan data available at the console or recon server, and sending the requested images back to the client where the request originated.

(c) The reviewer is provided a notification and a user interface to receive the images and view them at the review workstation.

In another embodiment, a prospective rescanning of a patient is enabled wherein a computer assisted rescanning of a patient while on the scanner to get high quality images through a FOI improves productivity by obviating the need for a recall of the patient. The prospective rescanning is, in one embodiment, implemented as follows.

(a) The rescan using an alternative imaging technique and/or acquisition parameters is triggered by a CAD algorithm that automatically detects FOIs and prescribes targeted rescans.

(b) The CAD algorithm may produce notifications to the operator of the CT Console with indication of anatomical FOI's that may need to be scanned at alternate technique.

(c) The operator may interactively acknowledge or reject recommendations made by the CAD algorithm for automated re-scan. For example, computer 36 accesses at least first image data from a first imaging system using a first scan prescription, processes the first image data in accordance with a CAD algorithm, prompts a user to prescribe a second scan prescription different than the first scan prescription based upon results of the CAD algorithm, and acquires at least second image data using the second scan prescription. In an exemplary embodiment, computer 36 provides recommendations regarding a second scan prescription based on the results of the CAD algorithm.

Method 100 includes prescribing an initial (first) scan 102, and checking if a Computer Aided Targeting (CAT) algorithm 104 (including a CAD algorithm) is on. When CAT 104 is on, computer 36 prompts a user to input a maximum number of hits (Nmax) or to accept a default Nmax. As used herein a hit refers to instances in which CAD 104 algorithm meets all criteria for what the CAD algorithm is looking for. Computer 36 then prompts the user to confirm 106 the received scan parameters. When CAT 104 is active, the prescribed scan is performed and the obtained data is submitted 108 to CAT 104. When CAT 104 is not active, the obtained data is saved 110. When N hits are generated 112 from CAT 104, different courses of action are performed dependent upon a comparison 114 of N to Nmax. When N is not greater than Nmax, the targeted data 116 (i.e., the original obtained data targeted by CAT 104) is used to reconstruct targeted images which are saved 118. When N is greater than Nmax, the user is informed of this and prompted with the choice of stopping and doing nothing, reconstructing all hits (i.e., reconstructing a plurality of targeted images based upon the CAT), and importing the targeted data into another application 120 such as a quantification application such as for example an Advanced Lung Analysis (ALA) program.

Technical effects of the herein described methods and apparatus include the potential for further enhancing the automation offered by CAD techniques by enabling either further processing image data or further acquisition of image data. In the case of processing, various parameters employed in post-processing of the acquired image data may be altered so as to render the reconstructed image more revealing or useful in identifying, localizing, and/or diagnosing a physiological condition. In particular, such parameters may include contrast, spatial resolution (e.g. zoom), color, and so forth. Moreover, the post-processing based upon the results of initial CAD evaluation may include mathematical evaluations such as segmentation, registration, computation of areas or volumes, and so forth. The "post-processing" may also involve the use of different reconstruction algorithms or different reconstruction parameters to generate images. For example, based on initial CAD results, different filter kernels (Soft, Standard, Detail, Bone, Edge, Lung, etc.) may be used to produce additional images from the original scan. Different filter kernels enhance different desired features in the image.

Other reconstruction parameters, such as reconstruction field-of-view, matrix size, targeting locations, etc. can also be modified to produce additional images based on the initial CAD results.

The initial CAD evaluation may also enable the automatic acquisition of subsequent images so as to enable a complete useful set of information to be gathered during a single patient session. The subsequent processing may be in order due, for example, to particular features that appear in images initially acquired but which are not adequately shown. Thus, the subsequent acquisition may include acquisition of data from other regions of the patient's body, at different orientations with respect to tissues of interest, at different resolution levels, and so forth. Moreover, entirely different acquired data may be desired based upon the initial CAD evaluation, such as data acquired via an entirely different modality system.

It should be noted that, as mentioned above, while initial images may be reconstructed and the CAD algorithm applied to the image data as described herein, the analysis may be partially or fully performed without such initial visualization. Thus, in case of CT image data, some or all of the CAD algorithm analysis may take place in Radon space. Ultimate useful image reconstruction may include visualizations of initial images, enhanced images, or both. The results of the CAD analysis may, where desired, even guide the type of image reconstruction performed, such as from Radon space in the CT imaging example.

By way of example, image data may be acquired from an X-ray system and the image data analyzed to identify a feature of potential interest. Images may be reconstructed based on the X-ray image data. Subsequent image acquisition may then be ordered via a CT system to provide a better view of the particular identified feature. One or more images may then be reconstructed based on the CT image data. As noted above, the actual image reconstruction based on the initial data may be optional, or at least distinct from the analysis performed by the CAD algorithm and the subsequent acquisition of the second image data.

Exemplary embodiments are described above in detail. The methods and apparatus are not limited to the specific embodiments described herein, but rather, components of each method and/or apparatus may be utilized independently and separately from other components described herein.

While the invention has been described in terms of various specific embodiments, those skilled in the art will recognize that the invention can be practiced with modification within the spirit and scope of the claims.

What is claimed is:

1. A method for a seamless display and analysis of dual resolution image data, said method comprising:
   reviewing image data of an object at low-resolution;
   performing a volumetric analysis of at least one feature of interest in the low-resolution image data;
   substituting high-resolution image data of the at least one feature of interest for the analyzed low-resolution image data without operator intervention;
   analyzing the high-resolution image data;
   linking the low-resolution image data to the high-resolution image data;
   displaying a volume rendering of the low-resolution image data;
   displaying analysis results of the high-resolution image data; and
   seamlessly accessing the analysis results of the high-resolution image data from the displayed volume rendering of the low-resolution image data within a single display.

2. A method in accordance with claim 1 further comprising selecting an area in the object represented by the high-resolution image data using a CAD algorithm.

3. A method in accordance with claim 1 wherein the high-resolution image data is present for only the features of interest identified by a CAD algorithm.

4. A method in accordance with claim 1 further comprising obtaining high-resolution image data representative of an area in an object for which high-resolution image data has not been obtained.

5. A computer readable medium for acquiring medical image data, said computer readable medium encoded with a computer program configured to:
   receive low-resolution image data;
   perform a volumetric analysis of at least one feature of interest in the low-resolution image data;
   substitute high-resolution image data for analyzed low-resolution image data without operator intervention;
   analyze the high-resolution image data;
   link the low-resolution image data to the high-resolution image data;
   display a volume rendering of the low-resolution image data;
   display analysis results of the high-resolution image data; and
   seamlessly access the analysis results of the high-resolution image data from the displayed volume rendering of the low-resolution image data within a single display.

6. A computer readable medium in accordance with claim 5, wherein said computer program is further configured to select an area in the object represented by the high-resolution image data using a CAD algorithm.

7. A computer readable medium in accordance with claim 5, wheein said computer program is further configured to present high-resolution data for only the features of interest identified by a CAD algorithm.

8. A computer readable medium in accordance with claim 5, wherein said computer program is further configured to obtain high-resolution data representative of an area in an object for which high-resolution data has not been obtained.

9. An imaging system comprising:
   a first image data acquisition system configured to acquire medical images; and
   a computer coupled to the image data acquisition system and configured to:
   receive low-resolution image data;
   perform a volumetric analysis of at least one feature of interest in the low-resolution image data;
   substitute high-resolution image data for the analyzed low-resolution image data without operator intervention;
   analyze the high-resolution image data;
   link the low-resolution image data to the high-resolution image data;
   display a volume rendering of the low-resolution image data;
   display analysis results of the high-resolution image data; and
   seamlessly access the analysis results of the high-resolution image data from the displayed volume rendering of the low-resolution image data within a single display.

10. An imaging system in accordance with claim 9 configured to select an area in the object is represented by the high-resolution image data using CAD algorithm.

11. An imaging system in accordance with claim 9 wherein the high-resolution image data is present for only the feature of interest identified by a CAD algorithm.

12. An imaging system in accordance with claim 9 further comprising a routine for obtaining high-resolution image data representative of an area in an object for which high resolution image data has not been obtained.

* * * * *